United States Patent [19]

Narato et al.

[11] 4,373,376

[45] Feb. 15, 1983

[54] METHOD AND APPARATUS FOR DIAGNOSING OVERHEATING OF AN ELECTRIC MACHINE

[75] Inventors: Kiyoshi Narato, Ibaraki; Keizo Ohtsuka; Sadahiko Niwa, both of Hitachi, all of Japan

[73] Assignee: Hitachi, Ltd., Tokyo, Japan

[21] Appl. No.: 188,096

[22] Filed: Sep. 17, 1980

[30] Foreign Application Priority Data

Sep. 17, 1979 [JP] Japan .................................. 54/117846

[51] Int. Cl.³ .............................................. G01N 31/08
[52] U.S. Cl. ........................................ 73/23.1; 73/116
[58] Field of Search .............. 73/116, 339 R, 23, 23.1, 73/28

[56] References Cited

U.S. PATENT DOCUMENTS 3,593,023 7/1971 Fullerton et al. ................... 73/23 X
3,916,671 11/1975 Carson et al. ....................... 73/23.1
4,279,142 7/1981 McIntire ............................. 73/1 G Primary Examiner—Jerry W. Myracle
Attorney, Agent, or Firm—Antonelli, Terry & Wands

[57] ABSTRACT

A method and apparatus for diagnosing an overheating of a gas-cooled type electric machine having at least some components coated with an organic insulating material which decomposes into, for example, particles when subjected to high temperatures. The apparatus includes an extracting arrangement for enabling an extraction of gas from any region in an interior space of the electric machine. A device is provided for detecting a density of the particles contained in the gas and an arrangement is provided for analyzing a composition of the decomposed organic insulating material in the coolant gas so that, at first, an overheat region may be found and, secondly, an overheat position in the overheat region can be determined on the basis of the organic composition of the decomposed organic insulating material contained in the coolant gas.

13 Claims, 2 Drawing Figures

METHOD AND APPARATUS FOR DIAGNOSING OVERHEATING OF AN ELECTRIC MACHINE

BACKGROUND OF THE INVENTION

The present invention relates to a method and apparatus for diagnosing overheating of a gas-cooling type electric machine and, more particularly, to an overheat diagnosing method and apparatus which enables a locating of an overheated coil or core in a gas-cooled type turbine generator by measuring a density of particles and analyzing the composition decomposed from varnish or resin insulation coated on the coil or core.

With the increasing capacity of electric machines such as, for example, turbine generators, there is an increased likelihood of an occurrence of a shortcircuit resulting from poor insulation in the generator thereby causing an unexpectedly great disaster. There is especially the high probability of the coil and core of the generator being damaged by heat. To prevent damages of electric machines such as turbine generators, an overheat diagnosing apparatus has been proposed in which an overheating of the coil or core of the electric machine is detected by measuring a density of particles decomposed from the insulating material, which insulating material is formed as a varnish or resin coated on the coil or core.

The operating principle of the above noted proposed overheating diagnosing apparatus is based on the fact that insulating material coated on the coil or core, when overheated, decomposes into small particles of the size of 0.001–1 micron. The particles spread or are suspended in the cooling gas used for cooling the coil or core which, in large turbine generators, is usually hydrogen. For the purpose of detecting an occurrence of overheating, a portion of the cooling gas is extracted from an interior of the turbine generator to enable a measurement of the density of the particles contained therein.

U.S. Pat. No. 3,427,880 provides an example of an overheat diagnosing apparatus of the aforementioned type wherein, an extracted gas is ionized and the negatively charged ions are detected as a current flowing in lead wire. However, a disadvantage of this proposed apparatus resides in the fact that the gas is extracted only from one end portion of the interior of the turbine generator and the extracted gas is detected to determine whether or not the gas includes particles. Consequently, an overheating at the other end portion of the interior of the generator is extremely difficult to detect. Moreover, even if an overheating is recognized or detected, with this proposed apparatus, it is impossible to determine the exact position of the overheating of the coil or core. Furthermore, if the detector of this proposed apparatus generates a fault signal due to a malfunctioning or unsatisfactory operation of the detector, the generator should be stopped although since it is the detector which is malfunctioning, such stoppage would naturally be unnecessary. Consequently, it is extremely desireable to provide a checking means for the detector so as to prevent the occurrence of unnecessary stoppages of the turbine generator.

The aim underlying the present invention essentially resides in providing an overheating method and diagnosing apparatus which enables a diagnosing of an exact overheating position on the coil or core in a gas-cooled type electric machine.

In accordance with advantageous features of the present invention, an overheat diagnosing apparatus is provided which includes means for selectively extracting a cooling gas from any one of a number of regions in an interior space of the electric machine, with means for detecting the density of the particles in the selectively extracted cooling gas whereby an overheat region of the machine is determined when the density of the particles in the region is higher than a predetermined level. Additionally, means are provided for analyzing the composition of the cooling gas from the selected overheat region whereby an overheat position in the selected overheat region is determined.

By virtue of the noted features of the present invention, the diagnosis of overheating is performed in two steps with the first step being that of detecting for selecting an overheating region including an overheating position and the second step being an analysis for finding out an exact overheating position by analyzing the compositions of the cooling gas.

In accordance with further features of the present invention, checking means are provided for enabling a checking of the detector of the diagnosing apparatus, with the checking means being capable of functioning or operating during the operation of the electric machine so that a stopping of the electric machines becomes totally unnecessary.

Advantageously, in accordance with the present invention, means are provided for controlling the extracting means, detecting means, and analyzing means so that the cooling gas in the selected overheat region is introduced into the analyzing means.

Preferably, the analyzing means in in the form of a gas chromatograph which is adapted to analyze the proportions of hydrocarbons contained in the cooling gas.

To facilitate the continuous monitoring of the overheat diagnosing apparatus and the electric machine, means are provided which display the results obtained in the detecting means and the analyzing means. Advantageously, a drain trap is provided for trapping water drops present in the extracted cooling gas which water droplets are condensed as the cooling gas is cooled to an ambient of room temperature.

Additionally, in order to verify the validity of the selection of the overheat region by the detecting means, in accordance with further features of the present invention, means are provided for checking the validity of such selection. Preferably, the checking means comprises a standard particle generator and a gas cylinder for supplying a carrier gas to carry the standard particles to the detecting means.

In accordance with advantageous features of the method of diagnosing overheating in a gas-cooled type electric machine, an interior space of the electric machine is divided into a plurality of regions, with a cooling gas being selectively extracted from any one of the regions. The density of the particles of organic insulating material in the extracted gas is then detected so that an overheat region including an overheat position is selected when the density of the particles in the region is higher than a predetermined level. The composition in the cooling gas from the selected overheat region is analyzed so that an overheat position in the selected overheat region is determined.

Advantageously, water drops in the extracted cooling gas are trapped and a validity of the selection of the overheat region is checked.

Accordingly, it is an object of the present invention to provide a method and apparatus for diagnosing overheating of a gas-cooled type electric machine which avoids, by simple means, shortcomings and disadvantages encountered in the prior art.

Another object of the present invention resides in providing an apparatus and method for diagnosing overheating of a gas-cooled type electric machine which considerably increases a reliability of a detector arrangement by providing a checking means for the detector.

Yet another object of the present invention resides in providing a method and apparatus for diagnosing overheating of a gas-cooled type electric machine by which it is possible to determine which regions in an interior space of the machine are overheated and to determine an exact position of the region being overheated by using a particle detector and a means for analyzing compositions contained in the gas.

A further object of the present invention resides in providing a method and apparatus for diagnosing overheating of gas-cooled type electric machines by which it is possible to confirm a validity of an overheat signal by checking detectors of the apparatus.

A still further object of the present invention resides in providing a method and apparatus for diagnosing overheating of a gas-cooled type electric machine which ensures a highly reliable diagnosis of the overheating.

Yet another object of the present invention resides in providing a method and apparatus for diagnosing overheating of a gas-cooled type electric machine by which it is possible to minimize damage to the electric machine caused by an overheating, to minimize the time necessary for repairing the machine, and to limit any adverse effect of overheating on the entire system of the plant.

A further object of the present invention resides in providing a method and apparatus for diagnosing overheating of a turbine generator which minimizes the number of times the generator has to be stopped to determine the presence of an overheating.

These and other objects, features, and advantages of the present invention will become more apparent from the following description when taken in connection with the accompanying drawings which show, for the purposes of illustration only, one embodiment in accordance with the present invention.

DETAILED DESCRIPTION OF THE PREFERRED EMBODIMENT

Figure 1:
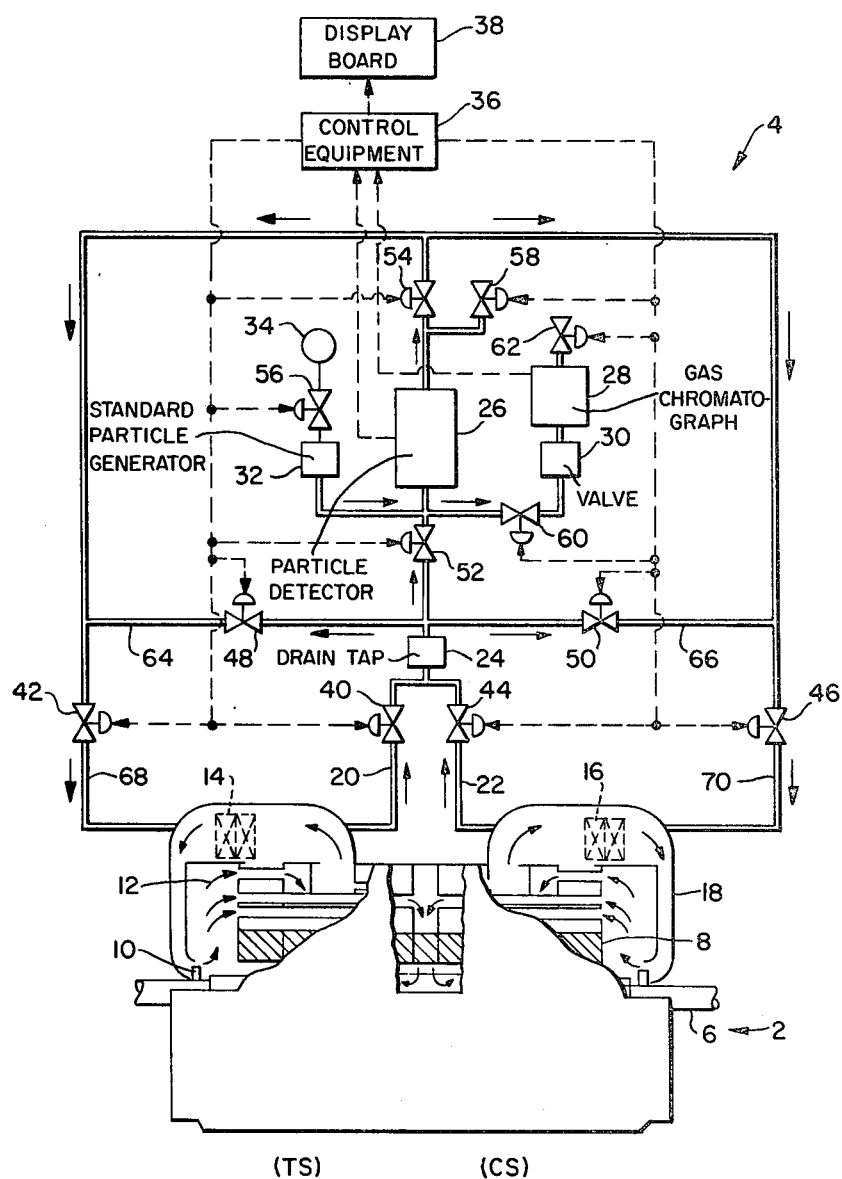
FIG. 1 is a schematic view of a turbine generator equipped with an overheat diagnosing apparatus in accordance with the present invention.

Referring now to the drawings wherein like reference numerals are used in both views to designate like parts and, more particularly, to FIG. 1, according to this Figure, a turbine generator generally designated by the reference numeral 2 is equipped with a diagnosing apparatus generally designated by the reference numeral 4. The turbine generator 2 includes a housing 18 which accommodates a rotor 6, a stator core 8 at a radial gap from the rotor 6, a fan 10 for producing a forced circulation of a coolant gas 12, and coolers 14, 16 for cooling the coolant gas 12.

In the embodiment illustrated in FIG. 1, the coolant gas 12 is extracted from a turbine side TS and a collector ring side CS of an interior space of the turbine generator 2. A pipe 20 is provided which enables an extracting of the coolant gas 12 from the turbine side TS and a pipe 22 enables an extraction of the coolant gas 12 from the collector ring side CS. A drain trap 24 is provided for trapping water drops in the extracted coolant gas 12.

A particle detector 26 is employed for detecting the presence of particles in the coolant gas 12 and for measuring a density of the particles in the gas 12. A gas chromatograph 28 analyzes, in a conventional manner, the proportions of hydrocarbons contained in the coolant gas 12. The hydrocarbons occur as a result of the decomposition of particles of insulation when such insulation is subjected to high temperatures. The gas chromatograph 28 measures the densities of the hydrocarbons and obtains a ratio of the hydrocarbons in the coolant gas 12. Since a ratio of the hydrocarbons contained in the coolant gas 12 depends upon the overheating position, by determining the ratio of hydrocarbons, the overheating position can be determined.

A valve 30 regulates the pressure of the coolant gas 12 entering the gas chromatograph 28 and a standard particle generator 32 checks whether the particle detector is functioning properly. For this purpose, a gas cylinder 34 is adapted to supply a carrier gas to carry the standard or known quantity of particles which would occur as the result of a predetermined heating and decomposing of predetermined amounts of various types of insulating material particles to the particle detector 26. Control or supervising equipment 36, of conventional construction, receives signals from the particle detector 26 and the gas chromatograph 28 with the control equipment sending or feeding the signals to a display board 38 which provides an instantaneous display of a condition of the turbine generator 2 as monitored by the control or supervisory equipment 36.

The control or supervisory equipment 36 controls, by way of appropriate signal conducting lines, all of the valves 40, 42, 44, 46, 48, 50, 52, 54, 56, 58, 60, 62, each of which are constructed as solenoid valves, so that the overheating diagnosing apparatus 4 operates in the manner described more fully hereinbelow in connection with the flow chart of FIG. 2.

Figure 2:
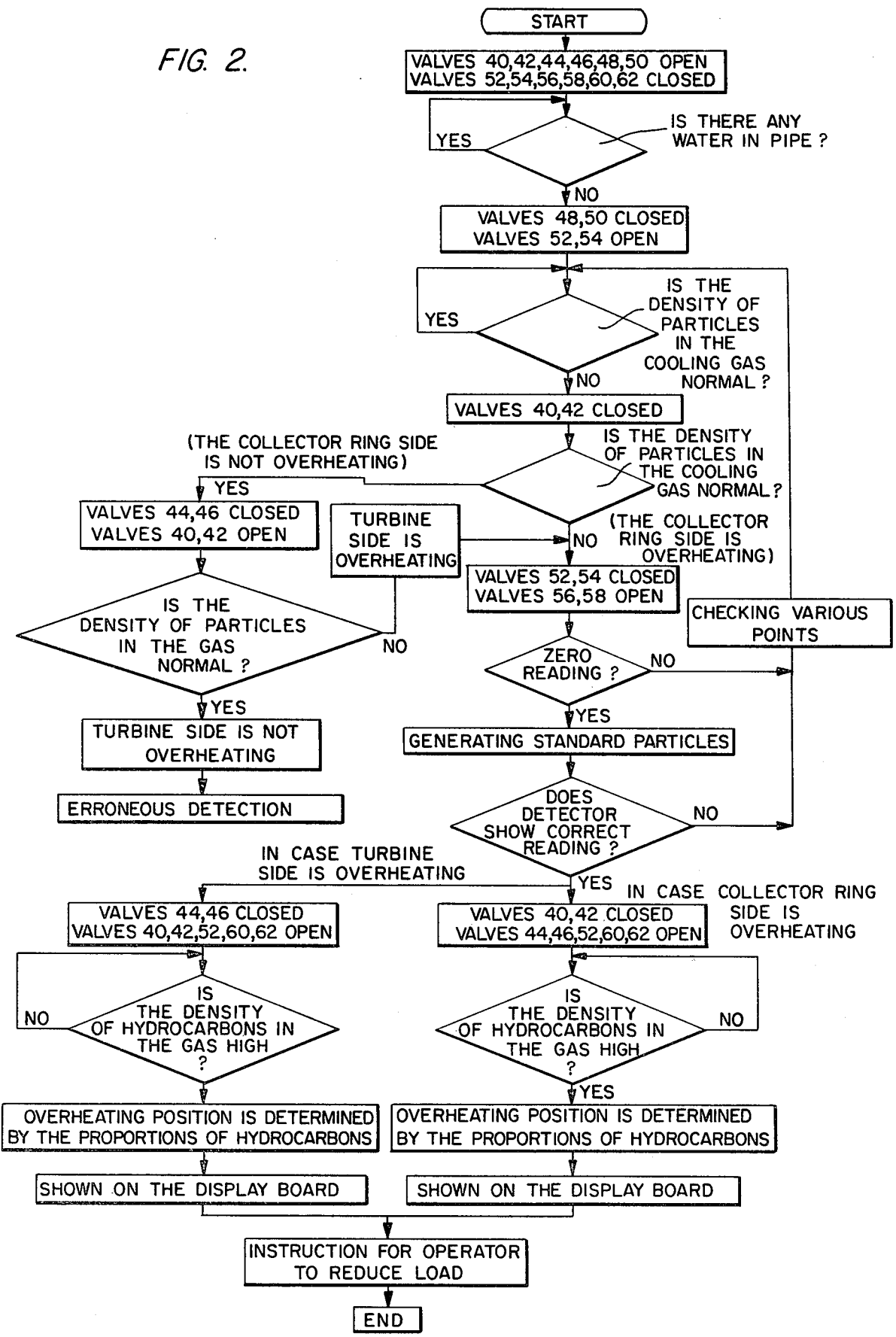
FIG. 2 is a flow chart showing a process of operation of the overheat diagnosing apparatus of FIG. 1.

As shown in FIG. 2, as well as can be seen from the flow of the coolant gas 12 in FIG. 1, the turbine generator 2 may be divided into two regions, namely, the collector ring side CS and the turbine side TS. The coolant gas 12 is extracted from the collector ring side CS and turbine side TS of the housing 18 through pipes or lines 20, 22 and solenoid valves 40, 44 and are fed to the drain trap 24. The coolant gas 12, at temperatures of 40°–50° C., is extracted from the housing 18 and the gas is cooled to the ambient or room temperature so that an excess amount of water vapor in the gas is condensed into water droplets which are caught by the drain trap 24. The coolant gas 12, from which the water drops have been removed, is returned to the housing 18 by way of bypass pipes or lines 64, 66, solenoid valves 48, 50 and return pipes or lines 68, 70. That is, since at the early stage of operation the solenoid valves 40, 42, 44, 46, 48, and 50 are opened and the solenoid valves 52, 54, 56, 58, 60, and 62 are closed, the extracted coolant gases 12 are not lead to the particle detector nor to the gas chromatograph 28.

The presence of the existence of water in the pipes is checked by noting the color of a silica gel. After the water drops have been removed from the coolant gas 12, the solenoid valves 48, 50 are closed and the solenoid valves 52, 54 are opened in orde to conduct the coolant gas 12 to and through the particle detector 26. The particle detector 26, in a conventional manner, continuously measures a density of the particles in the coolant gas 12 and generates a signal as to the density of the particles in the gas 12. The signal generated by the particle detector 26 is fed to the control or supervisory equipment 36, which monitors the entire system of the turbine generator 2 so as to enable a detecting of an overheating condition.

As long as no overheating condition occurs within the generator 2, the density of small particles, which is continuously monitored, is stable. When a certain portion or position of the turbine generator 2 is overheated, the density of the particles in the coolant gas 12 rises and a signal is generated by the particle detector 26 to that effect. The generated signal representing an increase in the density of the particles in the coolant gas 12 is fed to the control or supervisory equipment 36, with a signal then being supplied from the control or supervisory equipment 36 to the display board 38 so as to provide a visual indication of the occurrence of overheating in the turbine generator 2.

When the density of the particles becomes higher than a predetermined value, the control or supervisory equipment 36 identifies the generator as being in an overheated condition and then commences an overheat region evaluation process. In this process, the supervisory or control equipment 36 provides an output signal which closes the solenoid valves 40, 42 that lead the coolant gas 12 from the collector ring side CS to the particle detector 26. When the density of the particles detected by the particle detector 26 is below a predetermined valve, the generator 2 on the collector ring side CS is regarded as normal; however, if the density of particles detected by the particle detector 26 is higher than a predetermined value, the collector ring side CS is diagnosed as being overheated.

By a closing of the solenoid valves 44, 46 and an opening of the solenoid valves 40, 42, by appropriate signals from the supervisory or control equipment 36, the coolant gas 12 is conducted from the turbine side TS to the particle detector 26 to measure the density of the particles. If the density of the particles is higher than the predetermined value, the control or supervisory equipment 36 identifies the turbine side TS as being overheated. In this case, when the collecting ring side CS is normal, the diagnosing apparatus 4 of the present invention finally indicated on the display board 38 that the turbine side TS is overheated. When the collector ring side CS is also regarded as being overheated, the diagnosing apparatus 4 finally indicates on the display board 38 that both the collector side CS and turbine side TS are overheated.

After determining whether the collector ring side CS and/or the turbine side TS is overheated by means of the particle detector 26 detecting the density of the particles in the coolant gas, the diagnosing apparatus 4 then checks to determine whether the particle detector 26 is or is not functioning normally so as to thereby determine whether the signal generated by the particle detector 26 is or is not valid.

For the purposes of checking out the particle detector 26, the solenoid valves 52, 60 are closed and the solenoid valves 56, 58 are open so as to enable a supplying of a nitrogen gas from the gas cylinder 34 to the particle detector 26. The nitrogen gas is very pure and contains almost no particles so that the particle detector 26, in detecting the nitrogen gas, would show a zero reading. If the detector 26 does not show a zero reading, the detector 26 must be malfunctioning. If the particle detector 26 shows a zero reading, the standard density of particles are carried over by the nitrogen gas to the particle detector 26 in order to be certain that the detector 26 shows the correct density reading. The standard density of particles are generated by the standard particle generator 32. As noted above, the standard density may be determined by, for example, heating and decomposing certain predetermined amounts of insulating varnish. If the particle detector 26 does not show the correct reading for the standard or known density, the particle detector 26 must be considered to be malfunctioning and should be overriden and checked as in the case with the zero check.

When the particle detector 26 is found to be functioning properly, the diagnosing apparatus 4 indicates on the display board 38 that the signal from the particle detector 26 is valid and that an overheating condition in the generator 2 does in fact exist.

As described hereinabove, in the operation of detecting which region of the turbine 2 is overheating, i.e., the collector ring side CS and/or the turbine side TS, the respective solenoid valves are opened or closed to select a passage through which the coolant gas 12 is extracted and lead to the particle detector 26. After an overheating region of the turbine 2 is detected, the extracted gas is then analyzed by the gas chromatograph 28 to check the hydrocarbon contents in the gas in the following manner.

The solenoid valves 56, 58 are closed and the solenoid valves 52, 60, 62 are opened so as to enable a conducting of the coolant gas 12 from the collector ring side CS to the gas chromatograph 28 by way of the pipe or line 22, the solenoid valves 44, 52, 60 and the pressure regulating valve 30. After a predetermined amount of gas has been supplied to the gas chromatograph 28, the solenoid valve 60 is closed. The gas chromatograph 28, in a conventional manner, analyzes the coolant gas 12 to determine the proportions of nine hydrocarbons contained therein. The nine hydrocarbons are methan ($CH_4$), ethane, ($C_2H_6$), ethylene ($C_2H_4$), propane ($C_3H_8$), acetylene ($C_2H_2$), propylene ($C_3H_6$), normal butane ($nC_4H_{10}$), isobutane ($iC_4H_{10}$) and normal pentane ($nC_5H_{12}$). The gas chromatograph 28 generates signals by analyzing the above-noted hydrocarbons. The signals from the chromatograph 28 are then processed in the control or supervisory equipment 36 in order to determine the density of each of the hydrocarbon components and the ratio of the nine hydrocarbon components in the coolant gas 12. The hydrocarbon component ratio thus obtained is compared with a pre-stored hydrocarbon component ratio in the control or supervisory equipment 36 for each type of organic insulating material and the type and the position of the insulating material overheated and decomposed is determined.

Then the diagnosing apparatus 4 indicates on the display board 38 the position or region of the turbine generator 2 being overheated as well as the degree of overheating. The degree of overheating is determined from a density of particles and hydrocarbons. Upon the diagnosing apparatus 4 determining the existence of an overheating condition, the apparatus 4 then generates a signal for reducing the load on the generator 2.

While we have shown and described only one embodiment in accordance with the present invention, it is understood that the same is not limited thereto but is susceptible of numerous changes and modifications as known to one having ordinary skill in the art, and we therefore do not wish to be limited to the details shown and described herein, but intend to cover all such modifications as are encompassed by the scope of the appended claims.

We claim:

1. An overheat diagnosing apparatus for a gas-cooled type electric machine having at least some regions coated with an organic insulating material which decomposes when subjected to high temperatures, the apparatus comprising:
   means for selectively extracting a coolant gas from at least one region of an interior space of the electric machine;
   means for detecting a density of the decomposed organic insulating material in the selectively extracted coolant gas and for enabling a selection of an overheat region when the density of the decomposed organic insulating material in the coolant gas in the selected region is higher than a predetermined level;
   means for analyzing a composition of the decomposed organic insulating material in the coolant gas from a selected overheat region and for enabling a determination of an overheat position in the selected overheat region; and
   means for controlling said extracting means, said detecting means, and said analyzing means so that the coolant gas in the selected overheat region is introduced into said analyzing means.

2. The overheat diagnosing apparatus as set forth in claim 1, wherein said analyzing means is a gas chromatograph means for analyzing proportions of hydrocarbons contained in the coolant gas.

3. The overheat diagnosing apparatus as set forth in claim 1, further comprising means for displaying results obtained in said detecting means and said analyzing means.

4. The overheat diagnosing apparatus as set forth in claim 1, further comprising a drain trap means for trapping water drops in the extracted coolant gas.

5. The overheat diagnosing apparatus as set forth in claim 1, further comprising means for checking a validity of a selection of the overheat region by said detecting means.

6. The overheat diagnosing apparatus as set forth in claim 5, wherein said checking means comprises a standard particle generator and a gas cylinder for supplying a carrier gas to carry standard particles to said detecting means.

7. An overheat diagnosing apparatus for a gas cooled type electric machine having at least some regions coated with an organic insulating material which decomposes when subjected to high temperatures, the apparatus comprising:
   means for selectively extracting a coolant gas from any one of the regions in an interior space of the electric machine;
   means for detecting a density of the decomposed organic insulating material in the selectively extracted cooling gas and for enabling a selecting of an overheat region when the density of the decomposed organic insulating materials in the region is higher than a predetermined level;
   means for checking the validity of the selection of the overheat region by said detecting means; and
   means for analyzing proportions of hydrocarbons contained in the coolant gas from the selected overheat region and for enabling a determination of an overheat position in the selected overheat region.

8. A method of diagnosing an overheating in a gas-cooled type electric machine having at least some regions coated with organic insulating material which decompose when subjected to high temperatures, the method comprising the steps of dividing an interior space of the electric machine into a plurality of regions;
   selectively extracting a coolant gas from any one of the plurality of regions;
   detecting a density of the decomposed organic insulating material in the selectively extracted coolant gas and selecting an overheat region including an overheat position when the density of the decomposed organic insulating material in the selected region is higher than a predetermined level; and
   analyzing the composition of the decomposed organic insulating material in the coolant gas from the selected overheat region and determining an overheat position in the selected overheat region.

9. A method of diagnosing overheating in a gas-cooled type electric machine having at least some regions coated with an organic insulating material which decomposes when subjected to high temperatures, the method comprising the steps of:
   extracting a coolant gas from an interior space of the electric machine;
   detecting a density of the decomposed organic insulating material in the extracted coolant gas and providing an indication that the electric machine is overheating somewhere therein;
   dividing an interior space of the electric machine into a plurality of regions;
   selectively extracting a coolant gas from any one of the plurality of regions;
   detecting a density of the decomposed organic insulating material in the selectively extracted coolant gas and selecting an overheat region including an overheat position when the density of the decomposed organic insulating material in the region is higher than a predetermined level; and
   analyzing a composition of the decomposed organic insulating material in the coolant gas from the selected overheat region and determining an overheat position in the selected overheat region.

10. The method of one of claims 8 or 9 further comprising the step of:
    trapping water droplets in the extracted coolant gas after an extracting of the coolant gas from the interior space of the electric machine.

11. The method of one of claims 8 or 9, further comprising the step of:
    checking a validity of the selection of the overheat region after detecting the density of the organic insulating material in the selectively extracted coolant gas.

12. A method of diagnosing an overheating in a gas-cooled type electric machine having at least two regions therein coated with organic material which decompose when subjected to high temperature, said method comprising the steps of:

selectively extracting a coolant gas from each region in said machine;

detecting a density of the decomposed organic insulating material in the selectively extracted coolant gas and selecting an overheat region including an overheat position when the density of the decomposed organic insulating material in the selected region is higher than a predetermined level;

analyzing the composition of the decomposed organic insulating material in the coolant gas from the selected overheat region; and determining an overheat position in the selected overheat region.

13. A method of diagnosing an overheating region in a gas-cooled type electric machine, an interior space of the machine being coated with organic insulating material which decompose when subjected to high temperature, said method comprising the steps of:

dividing an interior space of the machine into at least two regions;

selectively extracting a coolant gas from each region of the at least two regions of the machine; and detecting a density of the decomposed organic insulating material in the selectively extracted coolant gas and selecting an overheat region when the density of the decomposed organic insulating material in the selected region is higher than a predetermined value.

* * * * *